US00PP17592P2

(12) United States Plant Patent
Trees

(10) Patent No.: US PP17,592 P2
(45) Date of Patent: Apr. 10, 2007

(54) ***NEMESIA* PLANT NAMED 'BALARWITE'**

(50) Latin Name: *Nemesia caerulea*
Varietal Denomination: Balarwite

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/283,301

(22) Filed: Nov. 18, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2005/2339 filed Nov. 16, 2005.

*Primary Examiner*—Kent Bell
*Assistant Examiner*—Annette H Para
(74) *Attorney, Agent, or Firm*—Audrey Charles

(57) ABSTRACT

A new and distinct cultivar of *Nemesia* plant named 'Balarwite' characterized by its white-colored flowers, floriferousness, and compact, upright growth habit.

1 Drawing Sheet

Latin name of genus and species of plant claimed: *Nemesia caerulea.*
Variety denomination: 'Balarwite'.

BACKGROUND OF THE INVENTION

The present invention relates to a new and distinct cultivar of *Nemesia* plant botanically known as *Nemesia caerulea* and hereinafter referred to by the cultivar name 'Balarwite'.

The new cultivar originated in a controlled breeding program in Arroyo Grande, Calif. during August 2002. The objective of the breeding program was the development of *Nemesia* cultivars with unique flower colors, continuous flowering, and a well-branched growth habit.

The new cultivar is the result of open pollination with the female (seed) parent being the proprietary *Nemesia caerulea* breeding selection designated NEM-214, not patented, characterized by its white-colored flowers, medium green-colored foliage, and medium upright growth habit. The male (pollen) parent of the new cultivar is unknown. The new *Nemesia* was discovered and selected by the inventor as a single flowering plant within the progeny of the above stated open-pollination during November 2002 in a controlled environment at Arroyo Grande, Calif.

Asexual reproduction of the new cultivar by terminal stem cuttings since November 2002 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balarwite' as a new and distinct cultivar of *Nemesia* plant:

1. White-colored flowers;
2. Floriferousness; and
3. Compact, upright growth habit.

Plants of the new cultivar differ from plants of the female parent primarily in growth habit.

Of the many commercially available *Nemesia* cultivars known to the inventor, the most similar in comparison to the new cultivar is 'Balarcomwhit', U.S. Plant Pat. No. 15,459. However, in side by side comparisons, plants of the new cultivar differ from plants of 'Balarcomwhit' in the following characteristic: Plants of the new cultivar are more compact than plants of 'Balarcomwhit' as measured by plant height, internode length, and pedicel length.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balarwite'. The plants were grown in 10 cm pots for 10 weeks in a greenhouse at West Chicago, Ill.

DETAILED BOTANICAL DESCRIPTION

Figure 1:
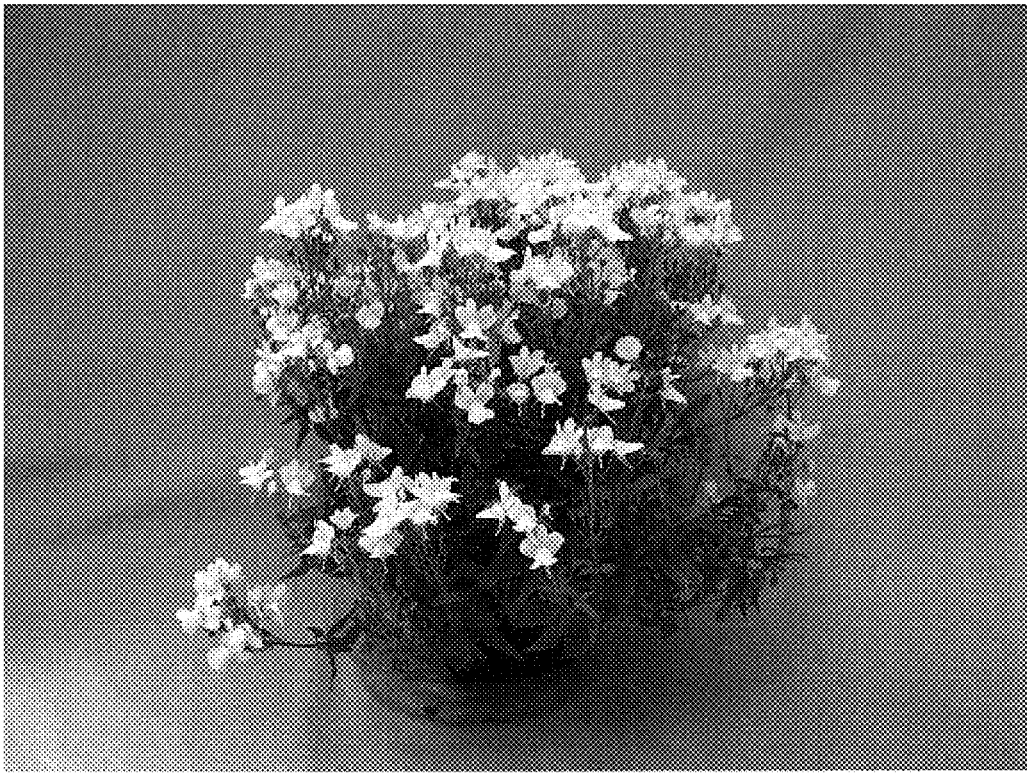
FIG. 1 illustrates a side view of the overall growth and flowering habit of 'Balarwite'.
Figure 2:
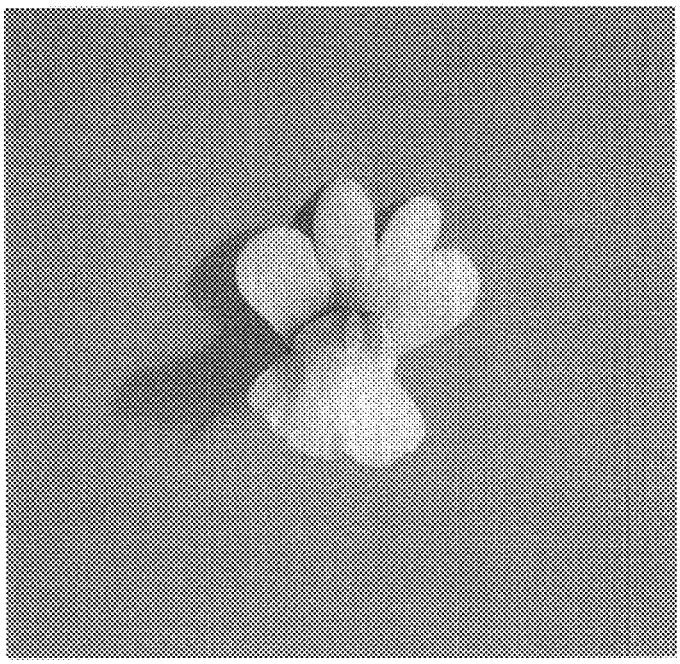
FIG. 2 illustrates a close-up view of a single flower of 'Balarwite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 4, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 10 weeks utilizing a soilless growth medium. Greenhouse temperatures were maintained at approximately 65° F. to 75° F. (18° C. to 24° C.) during the day and approximately 50° F. to 60° F. (10° C. to 15° C.) during the night. Greenhouse light levels of 4,000 to 7,000 footcandles were maintained during the day.

Botanical classification: *Nemesia caerulea* cultivar Balarwite.

Parentage:

*Female parent.*—Proprietary *Nemesia caerulea* breeding selection designated NEM-214, not patented.

*Male parent.*—Unknown.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fine and fibrous.

*Rooting habit.*—Branching.

Plant description:

*Crop time.*—Approximately 5 to 7 weeks from a rooted cutting.

*Growth habit and general appearance.*—Compact and upright.

*Size.*—Height from soil level to top of plant plane: Approximately 11.2 cm. Width: Approximately 25.5 cm.

*Branch.*—Quantity: Length: Approximately 3 primary branches with lateral branches potentially forming at every node. Strength: Moderate. Shape of all branches: Square in cross section. Length of primary branch: Approximately 11.3 cm. Diameter of primary branch: Approximately 1.3 mm. Texture: Glabrous. Color: 144B. Internode length at center of branch: Approximately 1.8 cm.

*Foliage.*—Number of leaves per main branch: Approximately 10. Fragrance: None. Form: Simple. Arrangement: Opposite. Aspect: At obtuse angle to stem. Shape: Ovate. Margin: Dentate. Apex: Acute. Base: Cordate. Venation pattern: Pinnate. Length of mature leaf: Approximately 2.7 cm. Width of mature leaf: Approximately 1.2 cm. Texture of upper surface: Puberulent. Texture of lower surface: Glabrous. Color of upper surface of young and mature foliage: 137A with venation of 144B. Color of lower surface of young and mature foliage: 138A with venation of 144B. Petiole length: Approximately 5.0 mm. Petiole diameter: Approximately 1.1 mm. Petiole texture: Glabrous. Petiole color: 144B.

Flowering description:

*Flowering habit.*—'Balarwite' is freely flowering under outdoor growing conditions with substantially continuous blooming from spring through autumn and year round in greenhouse environment.

*Time to first flower.*—Approximately 8 weeks from sticking of unrooted cutting.

*Lastingness of individual bloom.*—Approximately 7 to 10 days.

Inflorescence description:

*Type.*—Terminal raceme.

*Number per plant.*—Approximately 170 open racemes at 10 weeks.

*Number of fully open flowers per raceme.*—Approximately 4.

*Peduncle.*—Shape: Square in cross section. Strength: Strong. Aspect: Erect. Length: Approximately 1.7 cm. Diameter: Approximately 1.2 mm. Texture: Glabrous. Color: 154C.

Flower description:

*Bud rate of opening.*—Generally takes 3 days for bud to progress from first color to fully open flower.

*Bud just before opening.*—Shape: Ovate, including spur. Length including spur: Approximately 1.2 cm. Diameter: Approximately 6.0 mm. Color: 8D. Texture: Pubescent.

*Type.*—Solitary, zygomorphic, and bilabiate with nectar spur. Flowering is acropetally toward apex. Flowers are persistent with a strong, sweet fragrance.

*Flower size.*—Approximately 1.5 cm. Width: Approximately 1.4 cm. Depth, including nectar spur: Approximately 1.2 cm.

*Aspect.*—Facing outward.

*Petals.*—Quantity: 5 per flower. Arrangement: Four petals are fused at base forming an upper lip having two central lobes and one lateral lobe on each side. The fifth petal forms a lower lip that is modified into a nectar spur.

*Upper lip.*—Shape of all petals: Oblanceolate. Apex of all petals: Obtuse. Margin of all petals: Entire. Texture upper and lower surfaces of all petals: Glabrous. Color of upper and lower surfaces of all petals: Closest to 155D. Length of each central petal from throat: Approximately 6.9 mm. Width of each central petal: Approximately 3.4 mm. Length of each lateral petal from throat: Approximately 8.0 mm. Width of each lateral petal: Approximately 4.5 mm.

*Lower lip.*—Shape: Obovate. Apex: Emarginate. Margin: Entire, undulate. Length from palate: Approximately 5.5 mm. Width: Approximately 8.8 mm. Texture of upper and lower surfaces: Glabrous. Color of upper and lower surfaces: Closest to 155D. Palate length: Approximately 2.0 mm. Palate width: Approximately 2.2 mm. Palate color: 9A. Palate texture: Glabrous. Throat length: Approximately 5.0 mm. Throat width: Approximately 5.5 mm. Throat color: 5B in center with 155C along either side. Throat texture: Pubescent. Spur quantity: One per flower. Spur length: Approximately 4.6 mm. Spur diameter: Approximately 0.8 mm. Spur texture: Glabrous. Spur color: 12C at proximal end gradually transitioning to 1C at distal end.

*Pedicel.*—Strength: Strong, flexible. Aspect: Acute angle to stem. Length: Approximately 1.0 cm. Diameter: Approximately 0.6 mm. Texture: Densely pubescent. Color: 144A.

*Calyx.*—Shape: Cupped shaped, five-pointed star. Height: Approximately 3.5 mm. Width: Approximately 5.0 mm.

*Sepals.*—Quantity per flower: 5. Shape: Narrow elliptic. Apex: Acute. Margin: Entire. Sepal length: Approximately 3.5 mm. Sepal width: Approximately 0.9 mm. Texture of upper or inner surface: Glabrous. Texture of lower or outer surface: Densely pubescent. Color of upper and lower surfaces: 143B.

*Reproductive organs.*—Androecium: Stamen quantity: 4, curved around the pistil in two pairs. Stamen length: 2 are approximately 1.5 mm and 2 are approximately 2.0 mm. Filament color: Lighter than 155D. Anther shape: Ovate. Anther length: Approximately 0.7 mm. Anther color: 11A. Pollen amount: Moderate. Pollen color 12C. Gynoecium: Pistil quantity: One per flower. Pistil length: Approximately 2.0 mm. Stigma shape: Flat, oval. Stigma length: Approximately 0.1 mm. Stigma color: Lighter than 154D. Style length: Approximately 0.4 mm. Style color: 150D. Ovary length: Approximately 1.5 mm. Ovary texture: Glabrous. Ovary color: 145A.

Seed and fruit production: Neither seed nor fruit production has been observed.

Disease and pest resistance: Resistance to pathogens and pests common to *Nemesia* has not been observed.

What is claimed is:

1. A new and distinct cultivar of *Nemesia* plant named 'Balarwite', substantially as herein shown and described.

* * * * *